United States Patent
Kikuchi et al.

(10) Patent No.: US 9,962,186 B2
(45) Date of Patent: May 8, 2018

(54) TROCAR

(71) Applicant: OLYMPUS CORPORATION, Tokyo (JP)

(72) Inventors: Satoru Kikuchi, Tokyo (JP); Hiromu Ikeda, Tokyo (JP); Yasuhiro Miyazaki, Tokyo (JP); Hiroyoshi Kobayashi, Tokyo (JP); Masafumi Haraguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 231 days.

(21) Appl. No.: 14/718,450

(22) Filed: May 21, 2015

(65) Prior Publication Data

US 2015/0250498 A1    Sep. 10, 2015

Related U.S. Application Data

(63) Continuation of application No. PCT/JP2013/085332, filed on Dec. 25, 2013.
(Continued)

(51) Int. Cl.
| | | |
|---|---|---|
| *A61B 17/34* | (2006.01) | |
| *A61B 17/00* | (2006.01) | |
| *A61B 90/00* | (2016.01) | |

(52) U.S. Cl.
CPC .... *A61B 17/3421* (2013.01); *A61B 17/00234* (2013.01); *A61B 17/3417* (2013.01);
(Continued)

(58) Field of Classification Search
CPC ............ A61B 17/3421; A61B 17/3417; A61B 17/3462; A61B 17/00234;
(Continued)

(56) References Cited

U.S. PATENT DOCUMENTS

| | | |
|---|---|---|
| 4,874,378 A | 10/1989 | Hillstead |
| 5,634,908 A | 6/1997 | Loomas |

(Continued)

FOREIGN PATENT DOCUMENTS

| | | |
|---|---|---|
| CN | 102711635 A | 10/2012 |
| CN | 101959465 B | 12/2012 |

(Continued)

OTHER PUBLICATIONS

International Search Report and Written Opinion dated Feb. 18, 2014 issued in PCT/JP2013/085332.
(Continued)

*Primary Examiner* — Lauren P Farrar

(74) *Attorney, Agent, or Firm* — Scully, Scott, Murphy & Presser, P.C.

(57) ABSTRACT

A trocar including a distal-end tube portion that is disposed inside the body and has a first inner hole through which a medical device can be inserted; a proximal-end tube portion that is disposed outside the body and is connected to the distal-end tube portion, the proximal-end tube portion having a second inner hole that communicates with the first inner hole and has an axis which can be disposed in a direction not parallel to an axis of the first inner hole; and a movement facilitating portion that is disposed on at least one of the inner surface of the first inner hole and the inner surface of the second inner hole to facilitate the movement of the medical device inside the inner hole.

9 Claims, 12 Drawing Sheets

Related U.S. Application Data

(60) Provisional application No. 61/745,855, filed on Dec. 26, 2012.

(52) U.S. Cl.
CPC ............... *A61B 17/3462* (2013.01); *A61B 2017/00075* (2013.01); *A61B 2017/00318* (2013.01); *A61B 2017/00738* (2013.01); *A61B 2017/00845* (2013.01); *A61B 2017/3409* (2013.01); *A61B 2017/3447* (2013.01); *A61B 2017/3486* (2013.01); *A61B 2090/062* (2016.02)

(58) Field of Classification Search
CPC .... A61B 2017/00738; A61B 2090/062; A61B 2017/3409; A61B 2017/3447; A61B 2017/00318; A61B 2017/3486; A61B 2017/00845
See application file for complete search history.

(56) References Cited

U.S. PATENT DOCUMENTS

| | | | |
|---|---|---|---|
| 5,779,623 | A | 7/1998 | Bonnell |
| 6,554,793 | B1 | 4/2003 | Pauker et al. |
| 2003/0158576 | A1 | 8/2003 | Nagase et al. |
| 2003/0208103 | A1* | 11/2003 | Sonnenschein .... A61B 1/00154 |
| | | | 600/117 |
| 2004/0204682 | A1 | 10/2004 | Smith |
| 2010/0063362 | A1* | 3/2010 | Bonadio ............ A61B 17/0293 |
| | | | 600/203 |
| 2010/0331766 | A1 | 12/2010 | Hayakawa |
| 2011/0178508 | A1 | 7/2011 | Ullrich |
| 2012/0265214 | A1 | 10/2012 | Bender et al. |
| 2013/0197535 | A1* | 8/2013 | Okada ................ A61B 17/3421 |
| | | | 606/108 |

FOREIGN PATENT DOCUMENTS

| | | | |
|---|---|---|---|
| EP | 0638290 | A1 | 2/1995 |
| EP | 2 248 470 | A1 | 11/2010 |
| EP | 2248483 | A1 | 11/2010 |
| JP | H11-276425 | A | 10/1999 |
| JP | 2003-235857 | A | 8/2003 |
| JP | 4346615 | B2 | 10/2009 |
| JP | 2011-172787 | A | 9/2011 |
| JP | 2011-239975 | A | 12/2011 |
| WO | WO 99/51283 | A2 | 10/1999 |
| WO | WO 2006/100658 | A2 | 9/2006 |
| WO | WO 2011/037718 | A1 | 3/2011 |
| WO | 2011/088357 | A1 | 7/2011 |
| WO | WO 2011104937 | A1 * | 9/2011 ......... A61B 17/3421 |

OTHER PUBLICATIONS

Extended Supplementary European Search Report dated Jul. 15, 2016 in related European Application a 13 86 7606.9.

\* cited by examiner

TROCAR

CROSS-REFERENCE TO RELATED APPLICATIONS

This application is a continuation of PCT/JP2013/085332 filed on Dec. 25, 2013, which claims priority to U.S. Provisional Patent Application No. 61/745,855 filed on Dec. 26, 2012, the contents of each of which is incorporated herein by reference.

TECHNICAL FIELD

The present invention relates to trocars.

BACKGROUND ART

A known trocar in the related art is formed of two tube members that are connected so as to be able to swivel relative to each other (for example, see Patent Literature 1).

This trocar provides a wide working space even when a portion to be treated is located at a shallow position from a body surface, by placing the trocar through the body surface tissue of a patient such that a distal-end tube member is disposed inside the body and a proximal-end tube member is disposed outside the body, and by swiveling the distal-end tube member relative to the proximal-end tube member while a medical device, such as an endoscope, is inserted through the inner hole of the trocar.

PRIOR ART

Patent Literature

{Patent Literature 1} Japanese Unexamined Patent Application, Publication No. 2011-172787

SUMMARY OF INVENTION

An aspect of the present invention is a trocar including the following elements: a distal-end tube portion that is to be disposed inside a body and has a first inner hole through which a medical device can pass; a proximal-end tube portion that is to be disposed outside the body and is connected to the distal-end tube portion, the proximal-end tube portion having a second inner hole that communicates with the first inner hole and has an axis which can be disposed in a direction not parallel to an axis of the first inner hole; and a movement facilitating portion that is disposed on at least one of an inner surface of the first inner hole and an inner surface of the second inner hole to facilitate the movement of the medical device inside the inner hole.

DESCRIPTION OF EMBODIMENTS

A trocar 1 according to an embodiment of the present invention will be described below with reference to the drawings.

Figure 1:
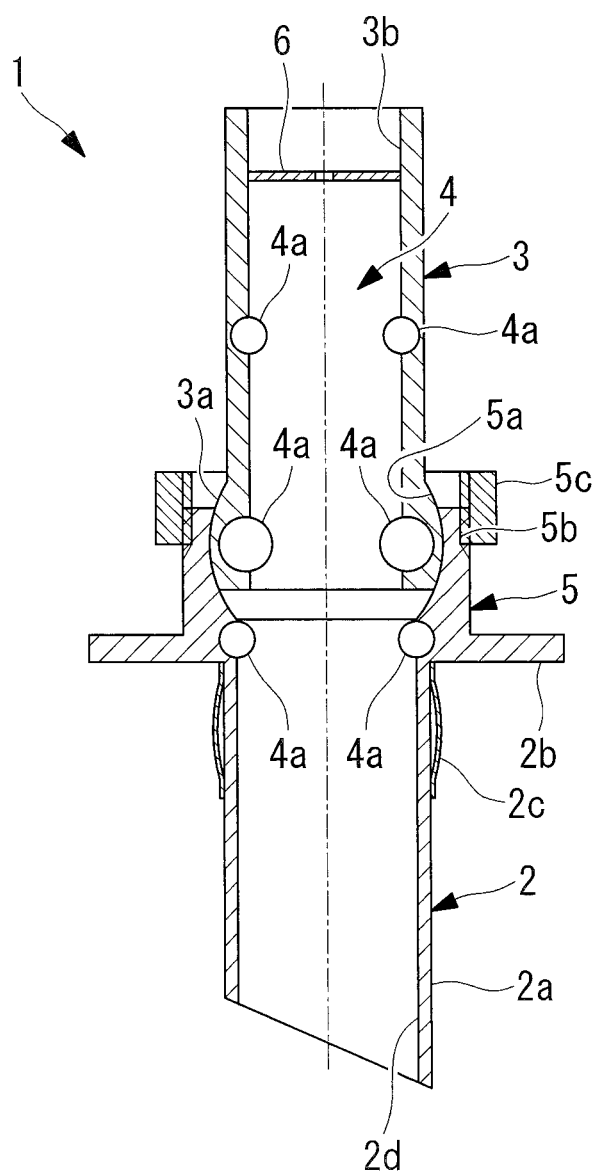
FIG. 1 is a longitudinal cross-sectional view showing a trocar according to an embodiment of the present invention.

As illustrated in FIG. 1, the trocar 1 according to this embodiment includes a distal-end tube portion 2, a proximal-end tube portion 3, and a movement facilitating portion 4.

The distal-end tube portion 2 includes the following elements: a tubular portion 2a that is to be inserted into the body from an opening provided in body surface tissue A of a patient; a flange portion 2b that is provided so as to project radially outward at the proximal-end side of the tubular portion 2a; a balloon 2c that can be inflated and deflated; and a fitting portion 5 to which the proximal-end tube portion 3 is fitted. The distal-end side of the tubular portion 2a has such a shape that it is cut obliquely with respect to the axis of the tubular portion 2a, so that it can be easily inserted into the body.

The tubular portion 2a has a first inner hole 2d penetrating the tubular portion 2a along the longitudinal axis thereof.

Figure 2:
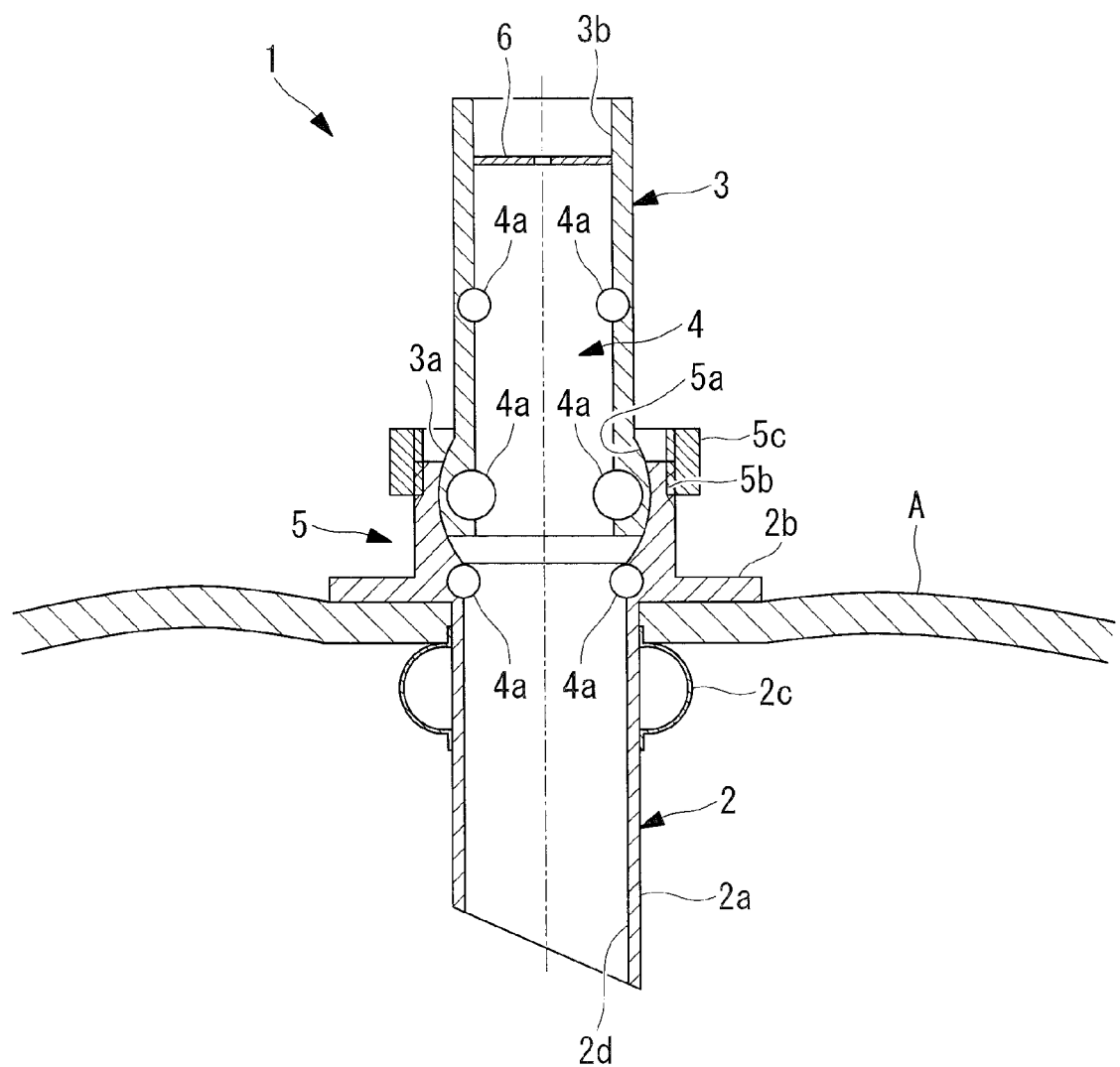
FIG. 2 is a longitudinal cross-sectional view showing a state in which the trocar in FIG. 1 is inserted into an opening in the skin and is fixed in place.

The flange portion 2b is formed larger than the opening provided in the body surface, so, when the tubular portion 2a is inserted into the body, the flange portion 2b comes into contact with the outer surface of the body surface tissue A, as illustrated in FIG. 2, preventing further insertion.

The balloon 2c is disposed at a position closer to the distal end than the flange portion 2b. The balloon 2c is deflated before being inserted, as illustrated in FIG. 1, and is inflated after being inserted into the body, as illustrated in FIG. 2. With this configuration, the balloon 2c nips the body surface tissue A together with the flange portion 2b, fixing the distal-end tube portion 2 so as not to be pulled out of the body.

The fitting portion 5 is disposed at a position closer to the proximal end than the flange portion 2b and has an inner spherical surface 5a that corresponds to a spherical portion 3a of the proximal-end tube portion 3 (described below). The outer surface of the fitting portion 5 has an external thread 5b. By fastening a nut 5c to the external thread 5b, the opening of the inner spherical surface 5a is held so as not to expand, preventing the spherical portion 3a from coming off from the inner spherical surface 5a.

The proximal-end tube portion 3 has a second inner hole 3b penetrating the proximal-end tube portion 3 along the longitudinal axis thereof and has, at the distal-end side, the spherical surface portion 3a that fits into the inner spherical surface 5a of the fitting portion 5 of the distal-end tube portion 2. A seal member 6 that can open or close the second inner hole 3b is disposed at the proximal-end side of the proximal-end tube portion 3. By fitting the spherical surface portion 3a into the inner spherical surface 5a, a spherical bearing is formed, enabling the proximal-end tube portion 3 to freely swivel about the center of the inner spherical surface 5a in any direction relative to the distal-end tube portion 2.

In the example shown in FIG. 1, the movement facilitating portion 4 is formed of a plurality of balls 4a that are rotatably supported on the inner surface of the proximal-end tube portion 3 and the inner surface of the distal-end tube portion 2. The plurality of balls 4a are disposed at intervals in the longitudinal direction and the circumferential direction.

The functions of the thus-configured trocar 1 according to this embodiment will be described below.

When percutaneous treatment is performed on an inside part of the body of a patient using the trocar 1 according to this embodiment, first, as illustrated in FIG. 1, the distal-end tube portion 2 of the trocar 1 is inserted, from the distal-end side, into an opening provided in the body surface tissue A of the patient, with the balloon 2c being deflated. By deflating the balloon 2c, the balloon 2c does not impede the insertion of the distal-end tube portion 2 into the body.

When the flange portion 2b of the distal-end tube portion 2 comes into contact with the surface of the body surface tissue A, as illustrated in FIG. 2, the balloon 2c is inflated. As a result, the body surface tissue A is nipped between the flange portion 2b and the balloon 2c, and the distal-end tube portion 2 is securely fixed to the body surface tissue A and is kept fixed to the body surface tissue A so as not to go into the body or be extracted from the body.

Figure 3:
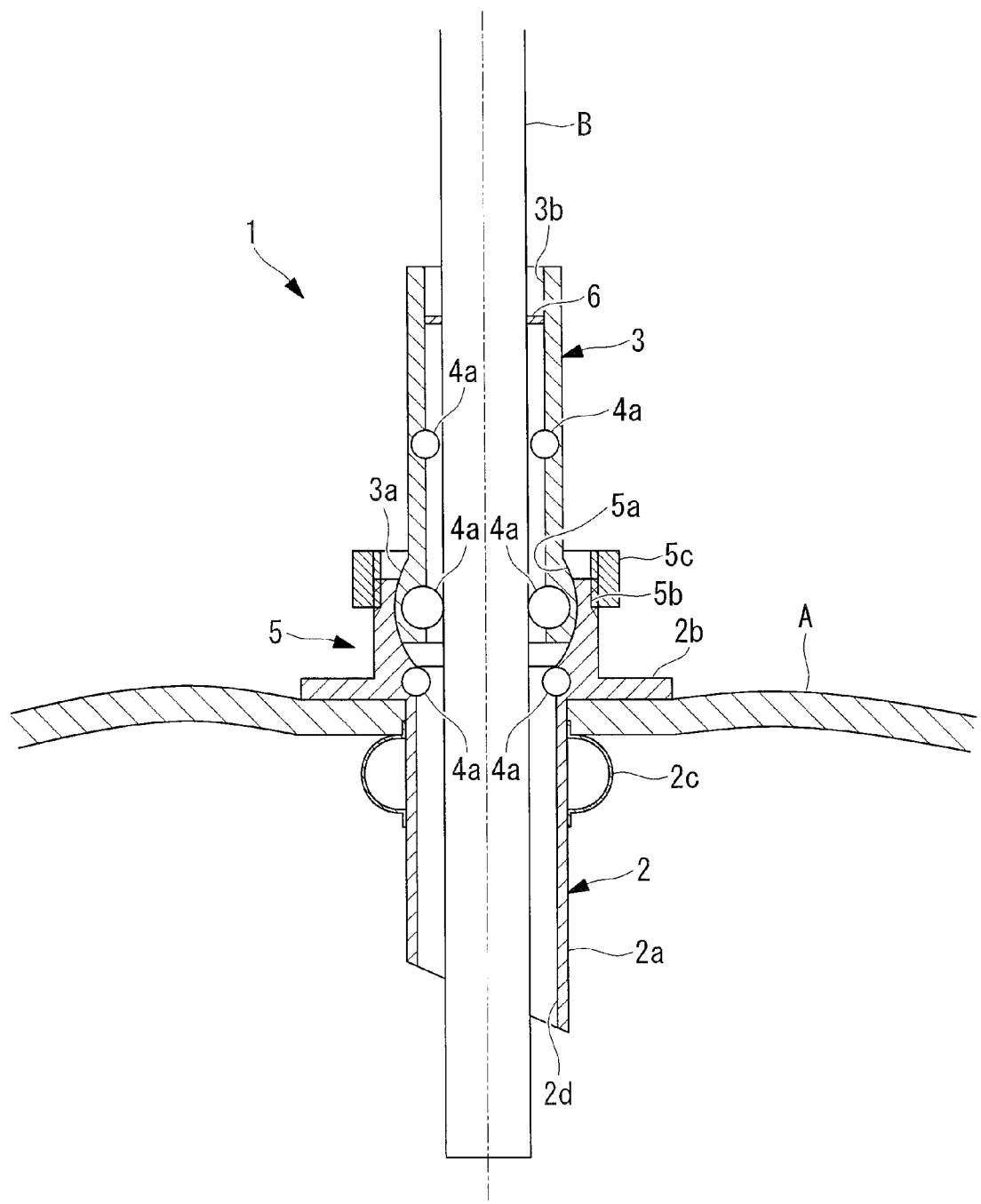
FIG. 3 is a longitudinal cross-sectional view showing a state in which a medical device is inserted into the trocar in FIG. 1.

In this state, a medical device B is inserted into the second inner hole 3b from an opening at the proximal end of the proximal-end tube portion 3. In the example shown in FIG. 3, a flexible endoscope, serving as the medical device B, is inserted. When the medical device B is inserted into the second inner hole 3b, the seal member 6 that has closed the second inner hole 3b is opened. While the medical device B is advanced through the second inner hole 3b and the first inner hole 2d, the seal member 6 keeps the space between the second inner hole 3b and the outer surface of the medical device B sealed.

Figure 4:
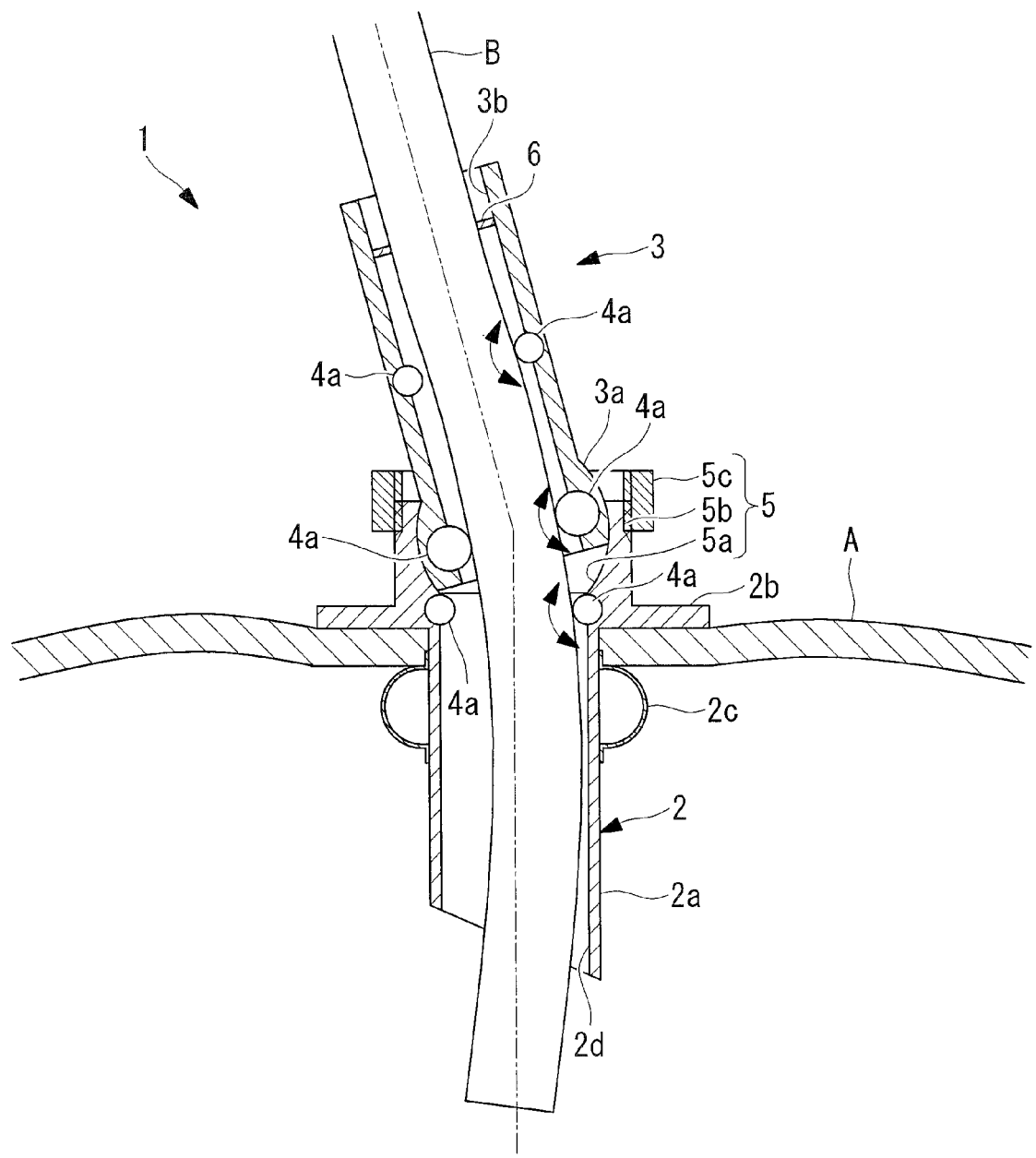
FIG. 4 is a longitudinal cross-sectional view showing a state in which a proximal-end tube portion of the trocar in FIG. 1 is swiveled relative to a distal-end tube portion.

When it is difficult to keep the insertion position of the medical device B outside the body, as illustrated in FIG. 4, the proximal-end tube portion 3 can be swiveled relative to the distal-end tube portion 2 fixed to the body surface tissue A to change the direction of the medical device B extends outside the body to a direction that eases the insertion. In this case, the medical device B is flexed inside the first inner hole 2d and the second inner hole 3b, and the outer surface thereof is urged against the inner surface of the first inner hole 2d and/or the inner surface of the second inner hole 3b.

However, because the trocar 1 according to this embodiment is provided with the movement facilitating portion 4 formed of the balls 4a that can rotate on the inner surfaces of the first inner hole 2d and the second inner hole 3b, the balls 4a come into contact with the outer surface of the medical device B. Accordingly, it is possible to achieve an advantage in that, when an external force that moves the medical device B in the longitudinal direction is applied to the medical device B or when an external force that rotates the medical device B about the longitudinal axis thereof is applied to the medical device B, the balls 4a are rotated between the outer surface of the medical device B and the inner surface of the first inner hole 2d and/or the inner surface of the second inner hole 3b, as shown in FIG. 4, reducing the friction between the medical device B and the inner holes 2d and 3b, and improving the maneuverability.

Although the balls 4a have been shown as an example of the movement facilitating portion 4 in this embodiment, the movement facilitating portion is not limited thereto, and it may be other rollable members, such as rollers. An advantage of using the balls 4a is that, because the balls 4a can rotate in any direction, they can facilitate the movement of the medical device B both in the longitudinal direction and about the longitudinal axis. The number and position of the balls 4a may be determined arbitrarily.

Furthermore, although the balls 4a are disposed both in the first inner hole 2d and the second inner hole 3b, the balls 4a may be disposed in only one of them.

Furthermore, although the case where the distal-end tube portion 2 and the proximal-end tube portion 3 can be swiveled relative to each other by rotating the spherical portion 3a in the inner spherical surface 5a has been shown as an example in this embodiment, instead of this, a case where the distal-end tube portion 2 and the proximal-end tube portion 3 are fixed with the axes of the inner holes 2d and 3b being inclined relative to each other can also be employed.

Furthermore, although the flexible endoscope has been shown as an example of the medical device B in this embodiment, the medical device B is not limited thereto, and it may be a forceps or the like that has, at a portion in the longitudinal direction, a flexible portion that can transmit pushing and pulling forces and a rotational force.

Furthermore, although the operation of the medical device B is passively facilitated by using the rollable members, such as the balls 4a in this embodiment, instead of this, as illustrated in FIGS. 5 to 8, a movement facilitating device 7 that actively facilitates the operation of the medical device B may be employed.

Figure 5:
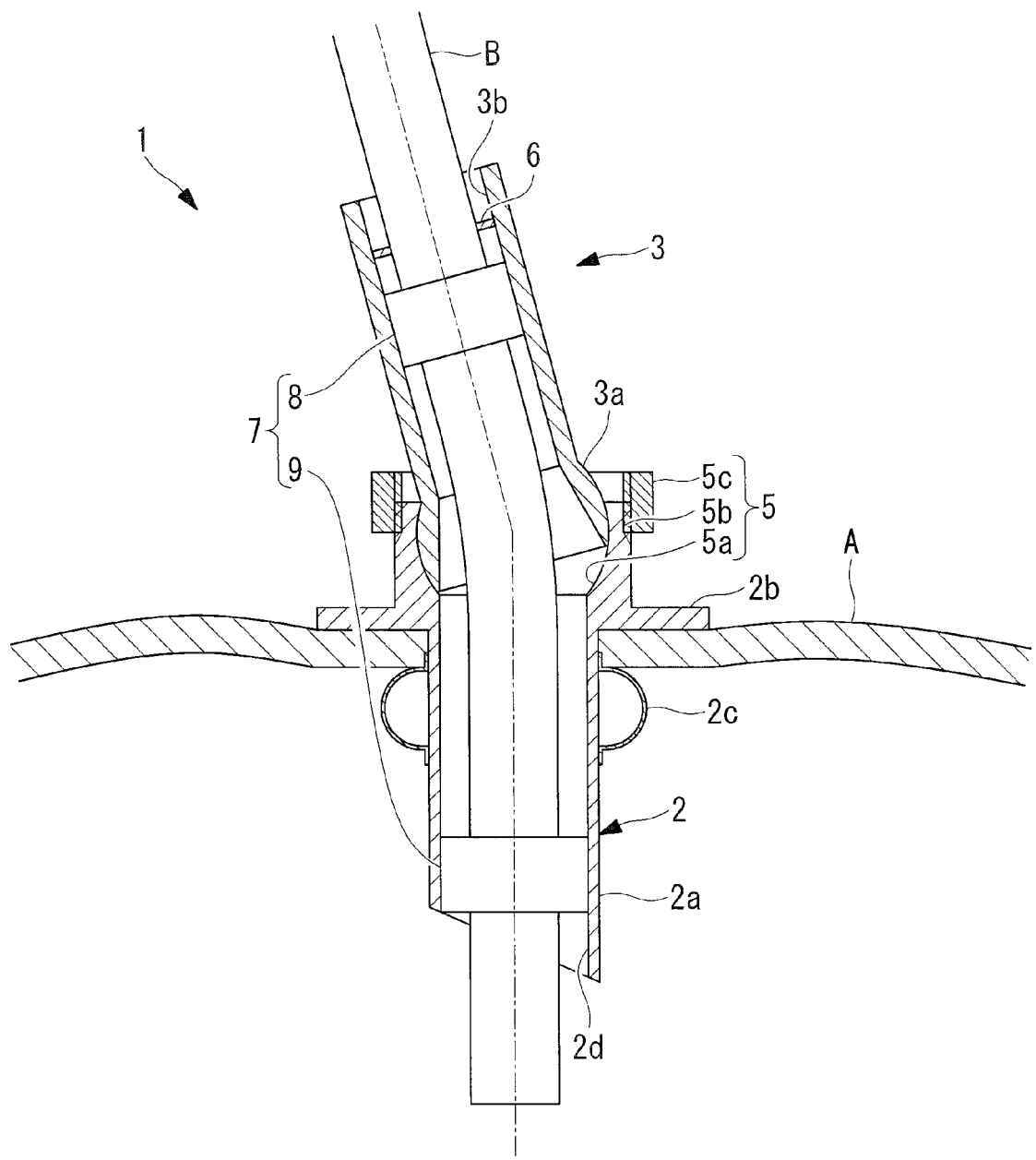
FIG. 5 is a longitudinal cross-sectional view showing a modification of the trocar in FIG. 1.

That is, in the example shown in FIG. 5, the movement facilitating portion 7 may include a movement detecting portion 8 that detects the movement of the medical device B and an device driving portion 9 that drives the medical device B according to the moving direction of the medical device B detected by the movement detecting portion 8.

Figure 6:
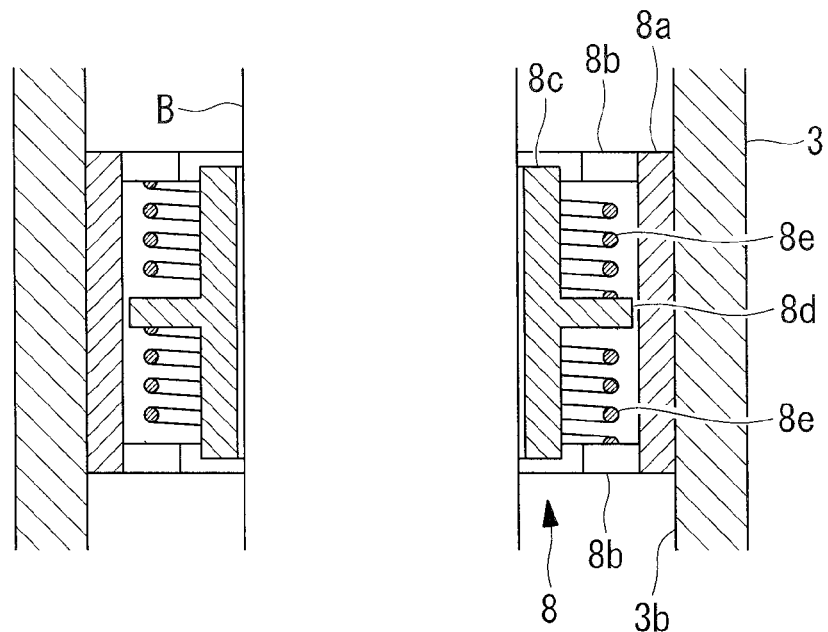
FIG. 6 is a longitudinal cross-sectional view showing a movement detecting portion of the trocar in FIG. 5.

As illustrated in FIG. 6, the movement detecting portion 8 includes the following elements: a casing 8a that is fixed to the inside of the second inner hole 3b in the proximal-end tube portion 3; ring-shaped load sensors 8b that are fixed at both ends, in the longitudinal direction, of the casing 8a; a tubular movable piece 8c to which the medical device B is loosely fitted; a flange-shaped portion 8d that extends radially outward from the middle portion of the movable piece 8c in the longitudinal direction; and two coil springs 8e that are disposed between the flange-shaped portion 8d and the two load sensors 8b.

While the medical device B is not operated, the movable piece 8c is supported at substantially the middle position in the longitudinal direction of the casing 8a by the coil springs 8e disposed on both sides of the flange-shaped portion 8d. At this time, the forces generated by the two coil springs 8e are balanced, and the two load sensors 8b detect substantially the same level of load.

Figure 8:
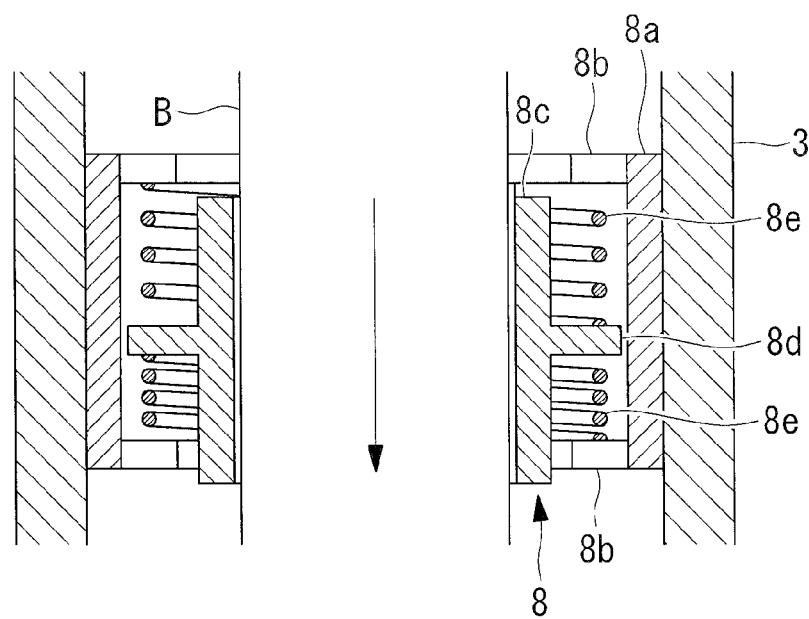
FIG. 8 is a longitudinal cross-sectional view for explaining a method of detecting movement of the medical device using the movement detecting portion in FIG. 6.

As illustrated in FIG. 8, when the medical device B is moved in the longitudinal direction, the movable piece 8c that is loosely fitted to the outer surface of the medical device B is moved in the same direction along with the movement of the medical device B, compressing the coil spring 8e disposed in front of the flange-shaped portion 8d in the moving direction and stretching the coil spring 8e disposed behind the flange-shaped portion 8d. As a result, the two load sensors 8b detect different loads, making it possible to know which direction the medical device B is being moved to.

Figure 7:
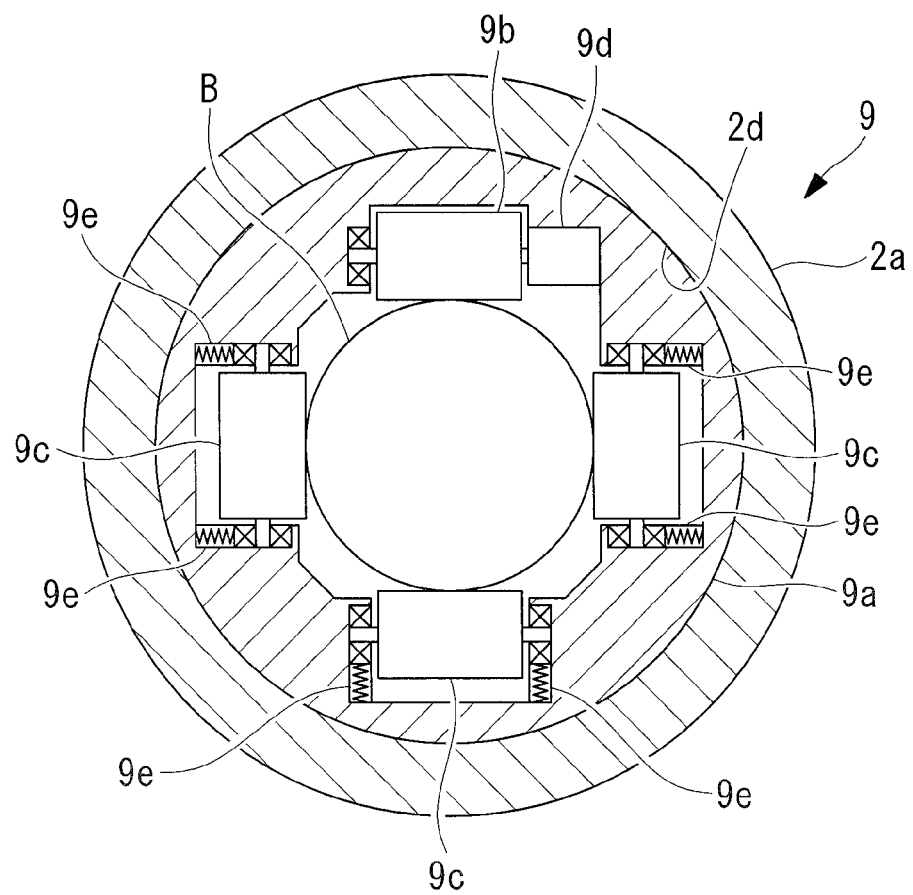
FIG. 7 is a lateral cross-sectional view showing a device driving portion of the trocar in FIG. 5.

On the other hand, as illustrated in FIG. 7, the device driving portion 9 includes a casing 9a that is fixed to the inside of the first inner hole 2d in the distal-end tube portion 2, and four rollers 9b and 9c that are rotatably attached to the casing 9a about axes extending in the directions perpendicular to the axis of the first inner hole 2d of the distal-end tube portion 2. The four rollers 9b and 9c are disposed at four positions at equal intervals in the circumferential direction of the medical device B.

One of the rollers 9b and 9c is the driving roller 9b, which is rotated by a motor 9d. The remaining three rollers are the driven rollers 9c, which are biased radially inward by springs 9e. That is, the medical device B is biased radially inward by the two driven rollers 9c facing each other, thereby being positioned at the center of the first inner hole 2d in one direction perpendicular to the axis of the first inner hole 2d. Furthermore, the medical device B is biased radially inward by the driven roller 9c facing the driving roller 9b, thereby being positioned at the center of the first inner hole 2d in another direction perpendicular to the axis of the first inner hole 2d.

Because the driven roller 9c facing the driving roller 9b biases the medical device B toward the driving roller 9b, the outer surface of the medical device B is pressed against the driving roller 9b. Thus, the driving force generated by the rotation of the driving roller 9b can be more reliably transmitted to the medical device B.

When the movement detecting portion 8 detects forward or backward movement of the medical device B in the longitudinal direction, the motor 9d for the driving roller 9b is driven to transmit to the medical device B a driving force in the same direction as the moving direction. This provides an advantage that the operation by an operator is facilitated, improving the maneuverability of the medical device B passing through the proximal-end tube portion 3 and the distal-end tube portion 2, which are disposed in a bent manner.

Figure 9:
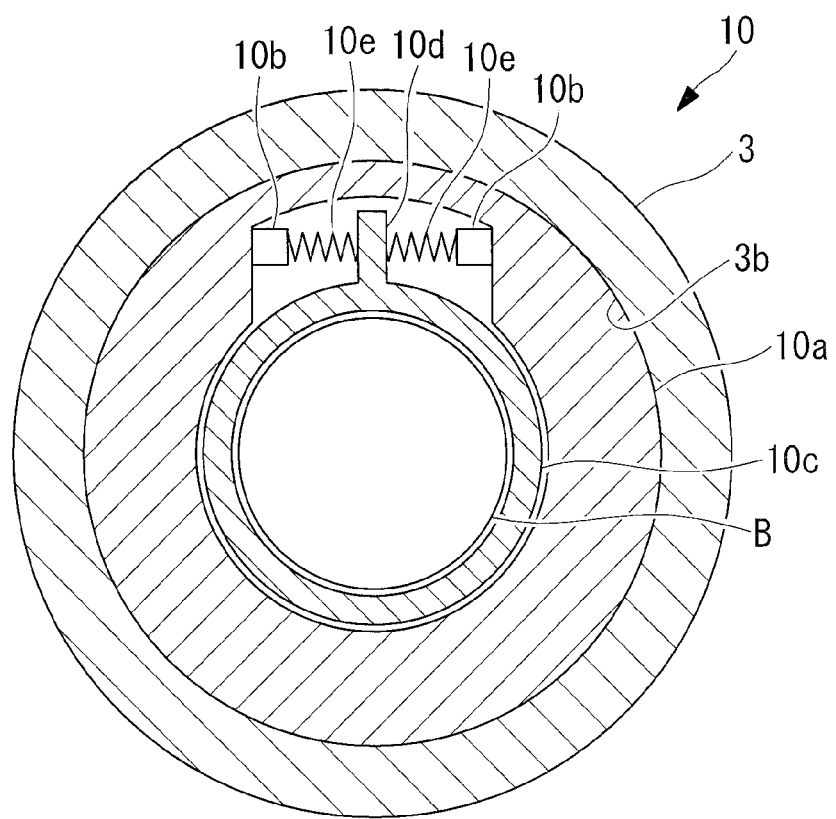
FIG. 9 is a lateral cross-sectional view showing another movement detecting portion of the trocar in FIG. 1.
Figure 10:
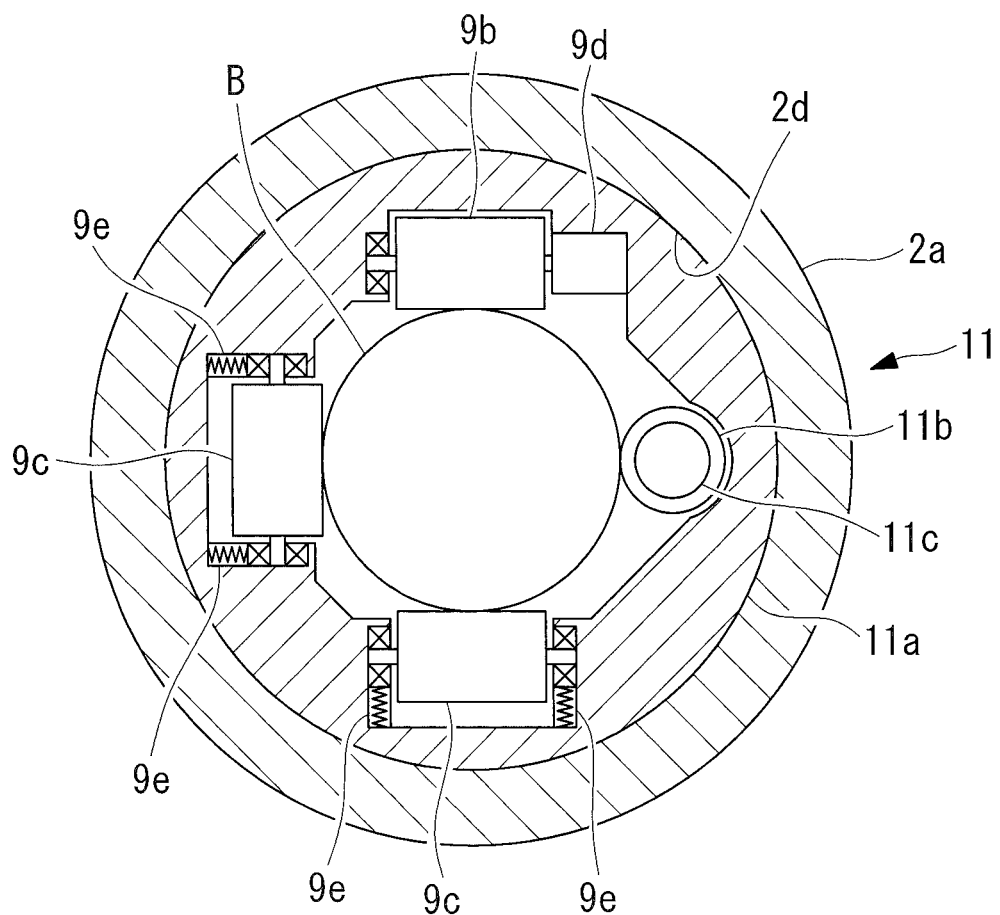
FIG. 10 is a longitudinal cross-sectional view showing a modification of the device driving portion in FIG. 8.

Although the movement facilitating portion 7, which facilitates the operation of the medical device B when moving the medical device B in the longitudinal direction, has been shown above as an example, the operation of the medical device B both in the longitudinal direction and about the longitudinal axis may be facilitated by adding a movement detecting portion 10, as shown in FIG. 9, and employing an device driving portion 11, as shown in FIG. 10.

More specifically, the movement detecting portion 10 shown in FIG. 9 includes the following elements: a casing 10a that is fixed to the inside of the second inner hole 3b in the proximal-end tube portion 3; two load sensors 10b that are disposed in the casing 10a with a space therebetween in the circumferential direction; a tubular movable piece 10c to which the medical device B is loosely fitted; a projecting portion 10d that extends radially outward from the outer circumferential surface of the movable piece 10c; and two coil springs 10e that are disposed between the projecting portion 10d and the two load sensors 10b.

When the medical device B is moved about the longitudinal axis, the movable piece 10c that is loosely fitted to the outer surface of the medical device B is moved in the same direction along with the movement of the medical device B, compressing the coil spring 10e disposed in front of the projecting portion 10d in the moving direction and stretching the coil spring 10e disposed behind the projecting portion 10d. As a result, the two load sensors 10b detect different loads, making it possible to know which direction the medical device B is being moved to.

On the other hand, as illustrated in FIG. 10, the device driving portion 11 includes the following elements: a casing 11a that is fixed to the inside of the first inner hole 2d in the distal-end tube portion 2; three rollers 9b and 9c that are attached to the casing 11a so as to be rotatable about axes extending in the directions perpendicular to the axis of the first inner hole 2d of the distal-end tube portion 2; and a roller 11b that is attached so as to be rotatable about an axis parallel to the axis of the first inner hole 2d.

The roller 11b also serves as a driving roller and is rotated by the motor 11c. The remaining three rollers are driven rollers 9c, which are biased radially inward by springs 9e. The medical device B is biased radially inward by the driven roller 9c facing the driving roller 11b, thereby being positioned at the center of the first inner hole 2d in the direction perpendicular to the axis of the first inner hole 2d.

Figure 11:
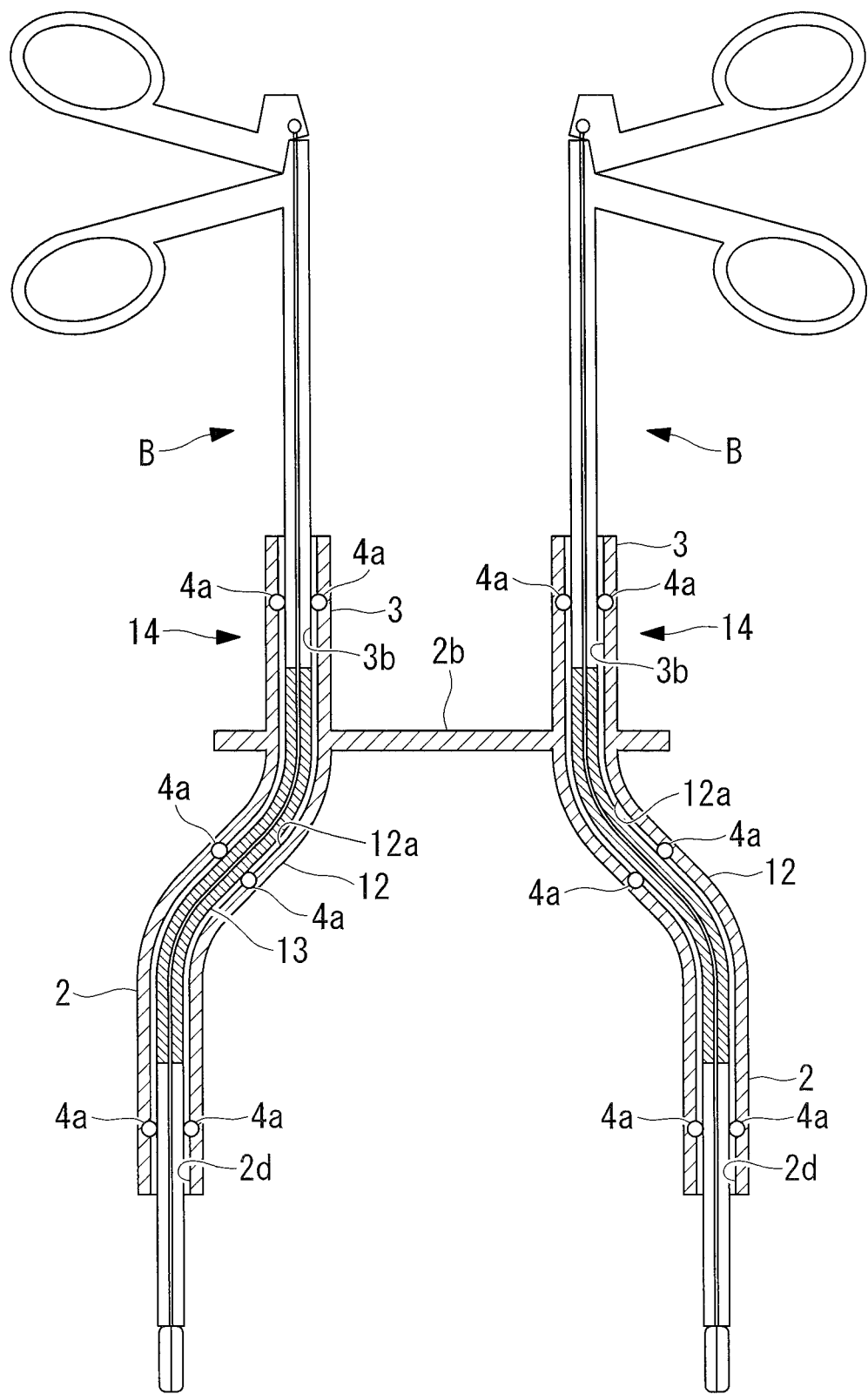
FIG. 11 is a longitudinal cross-sectional view of a modification of the trocar in FIG. 1, showing a state in which a forceps is inserted into the trocar having a connecting tube portion between the proximal-end tube portion and the distal-end tube portion.

Although the trocar 1 having one flexible portion has been used to give the explanation in this embodiment, as illustrated in FIG. 11, a connecting tube portion 12 that connects the distal-end tube portion 2 and the proximal-end tube portion 3, which are disposed substantially parallel to each other, and that has a third inner hole 12a communicating the first inner hole 2d with the second inner hole 3b may be provided between the distal-end tube portion 2 and the proximal-end tube portion 3. In the example shown in FIG. 11, a forceps having a flexible portion 13 at one position in the longitudinal direction (hereinbelow, forceps B) is shown as the medical device B. FIG. 11 shows a case where two trocars 14 are connected by the flange portion 2b.

This configuration allows the end of the forceps B to be disposed at a position different from the insertion position outside the body, while matching the moving direction of the forceps B on the outside of the body and the moving direction of the forceps B inside the body during the insertion operation. In this case, although the friction which is caused when the forceps B is moved inside the trocar 14 is larger than ones caused according to the above-described embodiments because there are two flexible portions, because the rotatable balls 4a are disposed on the inner surfaces of the distal-end tube portions 2, proximal-end tube portions 3, and connecting tube portions 12, as shown in FIG. 11, the friction which is caused when the forceps B is moved is reduced, significantly improving the maneuverability. The maneuverability can also be improved by providing other rollable members or the above-described movement facilitating portion 7, instead of the balls 4a.

Figure 12:
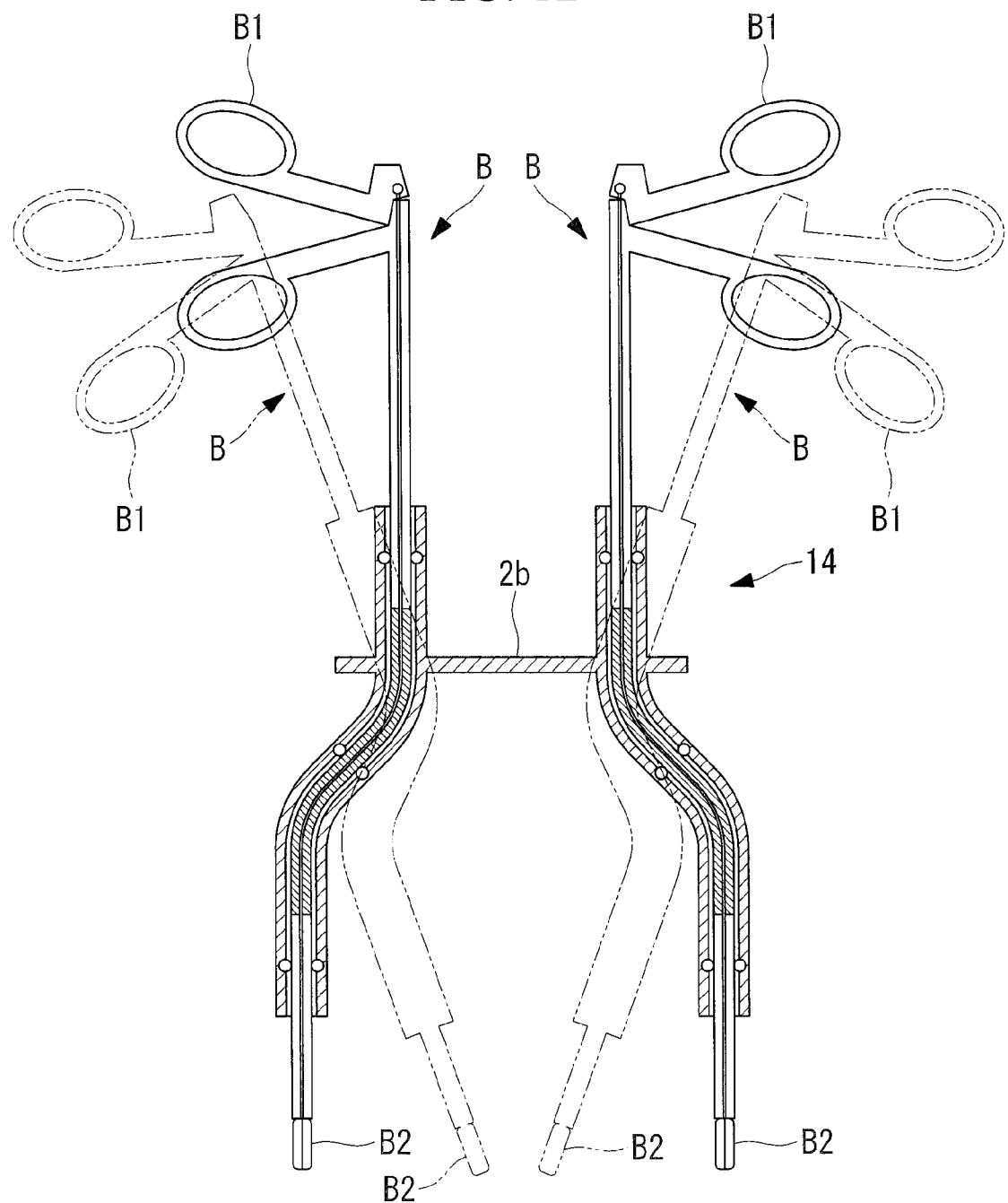
FIG. 12 is a longitudinal cross-sectional view showing a modification of the trocar in FIG. 11.

Furthermore, although the two trocars 14 are fixed to the flange portion 2b in FIG. 11, instead of this, as illustrated in FIG. 12, the two trocars 14 may be connected to the flange portion 2b so as to be able to swivel about the axis perpendicular to the longitudinal axis. This configuration enables the ends of the forceps B inside the body to approach each other, allowing efficient treatment on a diseased part located at a shallow position near the skin tissue A. In such a case, as illustrated in FIG. 12, by arranging grip ends B1 of the clamps B closer to each other than the other ends B2 of the forceps B, the distance between the grip ends B1 when the other ends B2 are brought toward each other, as shown by the dashed lines, does not increase too much. Thus, an operator can comfortably operate the forceps B.

Figure 13:
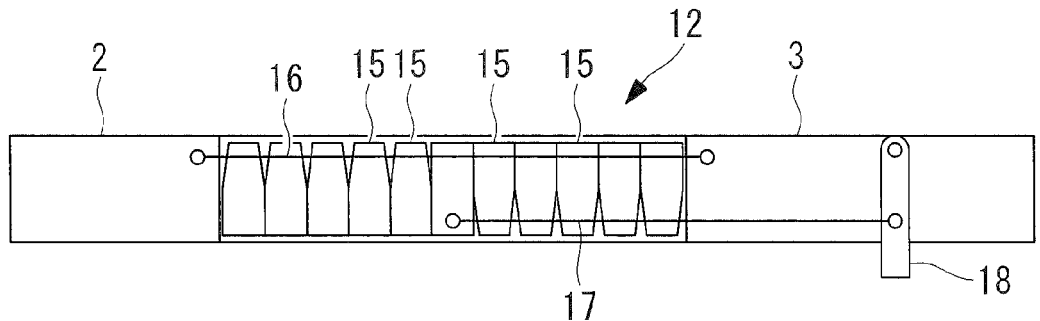
FIG. 13 is a side view showing a modification of the connecting tube portion of the trocar in FIG. 11.
Figure 14:
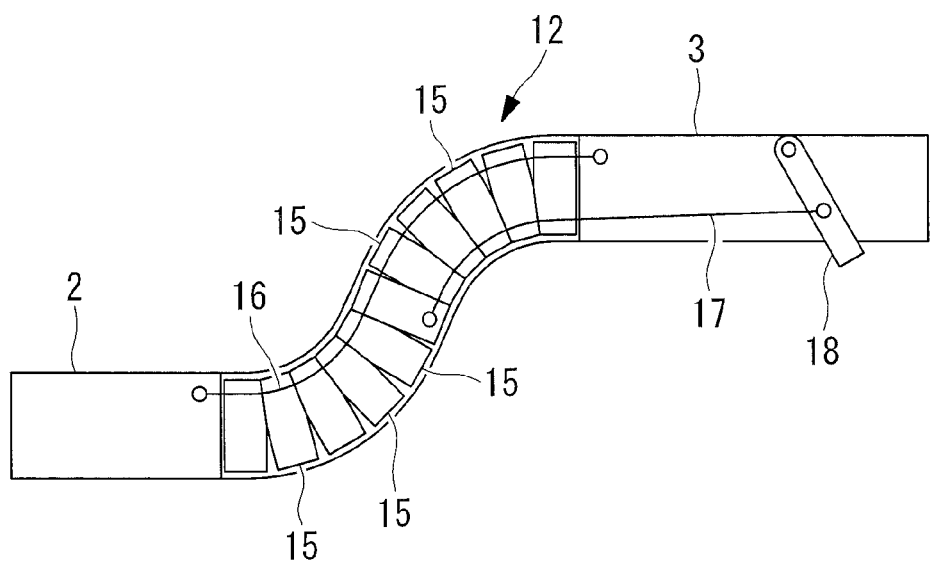
FIG. 14 is a side view showing a state in which the connecting tube portion in FIG. 13 is bent.

Furthermore, in the above-described embodiments, the connecting tube portion 12 may be made flexible. For example, as illustrated in FIGS. 13 and 14, the connecting tube portion 12 may have the following elements: a plurality of ring-shaped pieces 15 that can be swiveled relative to each other; a first wire 16 that connects the distal-end tube portion 2 and the proximal-end tube portion 3; a second wire 17 connected to the middle piece 15; and a lever 18 that is operated so as to change the tension of the second wire 17. By operating the lever 18, the shape of the connecting tube portion 12 may be changed from the straight-line shape, as shown in FIG. 13, to a substantially S-shape, as shown in FIG. 14. This configuration also can change the position where the end of the medical device B projects inside the body.

Figure 15:
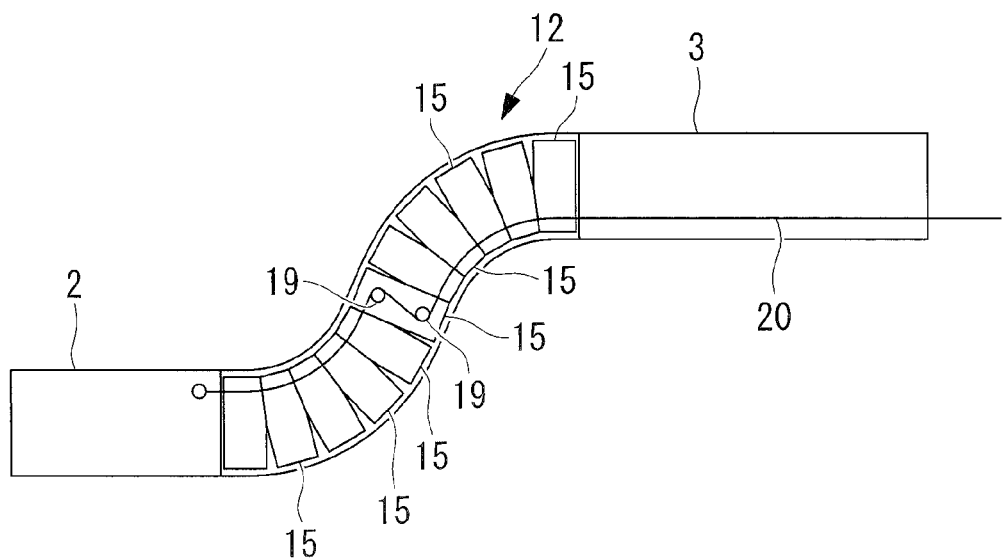
FIG. 15 is a side view showing a modification of the connecting tube portion in FIG. 13.

Alternatively, as illustrated in FIG. 15, the connecting tube portion 12 may be bent in a substantially S-shape by one wire 20 via pulleys 19 provided on the middle piece 15, instead of using the two wires 16 and 17.

Figure 16:
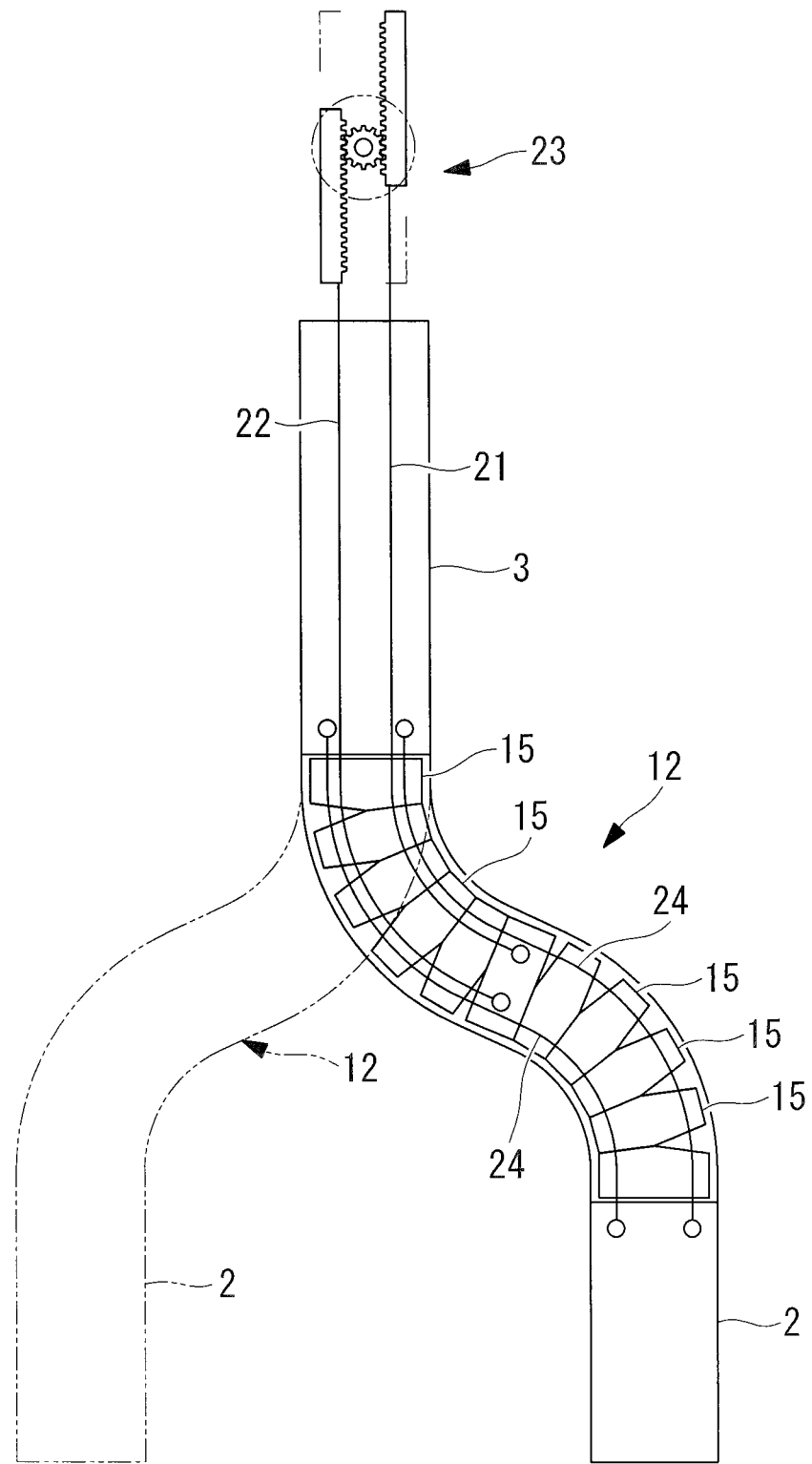
FIG. 16 is a side view showing a modification of the connecting tube portion in FIG. 13 and an angle-changing means therefor.

Alternatively, as illustrated in FIG. 16, by pushing or pulling two wires 21 and 22 connected to the middle piece 15 in an associated manner by a rack-and-pinion mechanism (angle-changing means) 23, the distal-end tube portion 2 and the proximal-end tube portion 3 arranged in a straight-line shape may be bent in two directions with a substantially S shape, as indicated by solid lines and dashed lines in FIG. 16. In FIG. 16, the reference numeral 24 denotes two wires connecting the distal-end tube portion 2 and the proximal-end tube portion 3.

The following inventions are derived from the aforementioned embodiment.

An aspect of the present invention is a trocar including the following elements: a distal-end tube portion that is to be disposed inside a body and has a first inner hole through which a medical device can pass; a proximal-end tube portion that is to be disposed outside the body and is connected to the distal-end tube portion, the proximal-end tube portion having a second inner hole that communicates with the first inner hole and has an axis which can be disposed in a direction not parallel to an axis of the first inner hole; and a movement facilitating portion that is disposed on at least one of an inner surface of the first inner hole and an inner surface of the second inner hole to facilitate the movement of the medical device inside the inner hole.

According to this aspect, when the distal-end tube portion is disposed inside the body and the proximal-end tube portion is disposed outside the body, and when the medical device is inserted into the first inner hole and the second inner hole whose axes are not parallel to each other, the movement facilitating portion disposed on at least one of the inner surfaces of the first inner hole and second inner hole facilitates the movement of the medical device inside the inner hole, improving the maneuverability thereof. That is, it is easy to move a bent medical device inside a trocar having a bent inner hole.

In the above-described aspect, the distal-end tube portion and the proximal-end tube portion may be connected such that the axis of the first inner hole and the axis of the second inner hole are inclined relative to each other.

With this configuration, when the medical device outside the body is moved along the axis of the first inner hole in the proximal-end tube portion, the medical device inside the body is moved in a direction intersecting the axis of the first inner hole, moving along the axis of the second inner hole in the distal-end tube portion. At this time, the movement facilitating portion facilitates the movement, enabling medical treatment with good maneuverability.

Furthermore, in the above-described aspect, the distal-end tube portion and the proximal-end tube portion may be connected such that a relative angle formed between the axis of the first inner hole and the axis of the second inner hole can be changed.

With this configuration, when the distal-end tube portion is disposed inside the body and the proximal-end tube portion is disposed outside the body, and when the medical device having a flexible portion is inserted into the second inner hole from outside the body, the medical device passes through the first inner hole and the third inner hole and is inserted into the body from the second inner hole, along an axis not parallel to the first inner hole. By changing the angle of the distal-end tube portion relative to the proximal-end tube portion, a wide working space can be obtained even when a portion to be treated is located at a shallow position from a body surface. At this time, the movement facilitating portion facilitates the movement of the medical device, enabling treatment with good maneuverability.

Furthermore, in the above-described aspect, the trocar may include the following elements: a connecting tube portion between the distal-end tube portion and the proximal-end tube portion, the connecting tube portion having a third inner hole communicating with the first inner hole and the second inner hole, wherein the connecting tube portion connects the distal-end tube portion and the proximal-end tube portion such that the axis of the first inner hole and the axis of the second inner hole are kept substantially parallel to each other.

With this configuration, when an operator operates the medical device, the insertion direction of the medical device outside the body and the insertion direction of the medical device inside the body becomes parallel. Thus, the medical device can be operated in the insertion direction which is intended by the operator.

Furthermore, in the above-described aspect, the shape of the connecting tube portion, in the longitudinal direction of the third inner hole, can be changed.

With this configuration, the direction in which the medical device extends inside the body can be easily changed while maintaining the substantially parallel relationship between the axis of the first inner hole and the axis of the second inner hole.

Furthermore, in the above-described aspect, the connecting tube portion may includes a plurality of pieces that are arranged in the longitudinal direction and are connected so as to swivel relative to one another, and an angle-changing means that changes the relative swivel angles between the pieces.

With this configuration, the shape of the third inner hole in the longitudinal direction can be easily changed by activating the angle-changing means to change the relative swivel angles between the plurality of pieces.

Furthermore, in the above-described aspect, the movement facilitating portion may be a rollable member rotatably supported on the inner surface.

With this configuration, when the medical device is moved inside the first inner hole and the second inner hole, the rollable member rolls on the surface of the medical device, reducing the friction between the medical device and the inner holes. Thus, the movement of the medical device is facilitated, enabling medical treatment with good maneuverability.

Furthermore, in the above-described aspect, the movement facilitating portion includes a movement detecting portion that detects a moving direction of the medical device in the first inner hole or the second inner hole, and an device driving portion that generates motive power in the moving direction of the medical device which is detected by the movement detecting portion so as to facilitate the movement of the medical device.

With this configuration, when the medical device is moved in the first inner hole or the second inner hole, the moving direction is detected by the movement detecting portion, and the device driving portion generates motive power in the direction which facilitates the movement. Thus, the medical device can be more easily moved in the direction in which it is intended to be moved, improving the maneuverability.

Furthermore, in the above-described aspect, the movement detecting portion may detect the moving direction, in the longitudinal direction, of the medical device inside the first inner hole or the second inner hole. The device driving portion may be a driving roller that rotates about an axis intersecting the longitudinal axis of the first inner hole or the second inner hole and that is configured to roll on the outer surface of the medical device.

With this configuration, when the medical device is moved in the longitudinal direction, the movement detecting portion detects the direction of the movement, and the driving roller is rotated so as to exert motive power in that direction. Thus, the driving roller is made to roll on the surface of the medical device, and the medical device is driven in the longitudinal direction which is meant by the operator, improving the maneuverability.

Furthermore, in the above-described aspect, the movement detecting portion may detect the moving direction, about the longitudinal axis, of the medical device inside the first inner hole or the second inner hole, and the device driving portion may be a driving roller that rotates about an axis parallel to the longitudinal axis of the first inner hole or the second inner hole and that is configured to roll on the outer surface of the medical device.

With this configuration, when the medical device is moved about the longitudinal axis, the movement detecting portion detects the direction of the movement, and the driving roller is rotated so as to exert motive power in that direction. Thus, the driving roller is made to roll on the surface of the medical device, and the medical device is driven about the longitudinal axis which is meant by the operator, thus improving the maneuverability.

The above described embodiments achieve an effect of enabling a wide working space even when a portion to be treated is located at a shallow position from the body surface, and improving the maneuverability.

EXPLANATION OF REFERENCE

B forceps (medical device)
1, 14 trocar
2 distal-end tube portion
2d first inner hole
3 proximal-end tube portion
3b second inner hole
4, 7 moving facilitating portion
4a bass
8, 10 movement detecting portion
9, 11 device driving portion
9b driving roller
11b driving roller
12 connecting tube portion
12a third inner hole
15 ring-shaped piece
16, 17, 20, 21, 22, 24 wire
18 lever
19 pulley
23 rack-and-pinion mechanism

The invention claimed is:

1. A trocar comprising:
a distal-end tube portion that is to be disposed inside a body and has a first inner hole through which a medical device can pass;
a proximal-end tube portion that is to be disposed outside the body and is connected to the distal-end tube portion, the proximal-end tube portion having a second inner hole that communicates with the first inner hole, the proximal-end tube portion being movable relative to the distal-end tube portion between a first position where the first inner hole has an axis parallel with an axis of the second inner hole and a second position where the axis of the second inner hole intersects with the axis of the first inner hole; and
a movement facilitating portion that is disposed on at least one of an inner surface of the first inner hole and an inner surface of the second inner hole, at least a portion of the movement facilitating portion only engaging a medical device inserted through the first and second inner holes when the distal-end tube portion and proximal-end tube portion are in the second position to facilitate the movement of the medical device inside the at least one of the first and second inner holes;
wherein the movement facilitating portion comprises at least one rollable member rotatably supported on at least one of the inner surface of the first inner hole or the inner surface of the second inner hole.

2. The trocar according to claim 1, wherein the distal-end tube portion and the proximal-end tube portion are connected such that the axis of the first inner hole and the axis of the second inner hole are inclined relative to each other.

3. The trocar according to claim 1, wherein the distal-end tube portion and the proximal-end tube portion are connected such that a relative angle formed between the axis of the first inner hole and the axis of the second inner hole can be changed.

4. The trocar according to claim 1, comprising a connecting tube portion between the distal-end tube portion and the proximal-end tube portion, the connecting tube portion having a third inner hole communicating with the first inner hole and the second inner hole, wherein the connecting tube portion connects the distal-end tube portion and the proximal-end tube portion such that the axis of the first inner hole and the axis of the second inner hole are kept substantially parallel to each other.

5. The trocar according to claim 4, wherein the shape of the connecting tube portion, in the longitudinal direction of the third inner hole, can be changed.

6. The trocar according to claim 5, wherein the connecting tube portion includes a plurality of pieces that are arranged in the longitudinal direction and are connected so as to swivel relative to one another, and a wire connected to at least one of the pieces, wherein applying tension to the wire changes the relative swivel angles between the pieces.

7. The trocar according to claim 1, wherein the movement facilitating portion further includes a movement detecting portion that detects a moving direction of the medical device in the first inner hole or the second inner hole, and a motor that drives the at least one rollable member in the moving direction of the medical device which is detected by the movement detecting portion.

8. The trocar according to claim 7, wherein
the movement detecting portion detects the moving direction of the medical device inside the first inner hole or the second inner hole, the moving direction being along the longitudinal direction; and
the motor is configured to rotate the at least one rollable member about an axis intersecting the longitudinal axis of the first inner hole or the second inner hole so that the at least one rollable member rolls on an outer surface of the medical device.

9. The trocar according to claim 7, wherein
the movement detecting portion detects the moving direction of the medical device inside the first inner hole or the second inner hole, the moving direction being about the longitudinal axis; and
the motor device driving portion is configured to rotate the at least one rollable member about an axis parallel to the longitudinal axis of the first inner hole or the second inner hole so that the at least one rollable member rolls on an outer surface of the medical device.

* * * * *